United States Patent [19]

Shum et al.

[11] Patent Number: 4,612,390

[45] Date of Patent: Sep. 16, 1986

[54] METHOD FOR PRODUCING BRANCHED CARBONYLATION PRODUCTS FROM ALPHA UNSATURATED OLEFINS

[75] Inventors: Wilfred P. Shum, Swarthmore; John F. White, Villanova, both of Pa.

[73] Assignee: Atlantic Richfield Company, Los Angeles, Calif.

[21] Appl. No.: 361,311

[22] Filed: Mar. 24, 1982

[51] Int. Cl.$^4$ .................. C07C 51/14; C07C 67/38
[52] U.S. Cl. .................. 562/522; 260/410.9 R; 260/413; 560/233
[58] Field of Search ......... 562/522; 260/413, 410.9 R, 260/410.9; 560/233

[56] References Cited

U.S. PATENT DOCUMENTS 4,257,973  3/1981  Mrowca .................. 562/522
4,292,437  9/1981  Squire et al. .................. 560/233

OTHER PUBLICATIONS

Tolman, C. A., Chemical Reviews, 77:3, pp. 313–348, (1977).

*Primary Examiner*—Werren B. Lone
*Attorney, Agent, or Firm*—Michael S. Jarosz

[57] ABSTRACT

A novel method for producing branched carboxylic acids or esters from alpha-unsaturated olefins is disclosed. Such olefins are reacted with a novel, sterically hindered, ortho substituted phenylphosphine palladium halide catalysts in the presence of water or primary or secondary alcohols to produce high branched end product yields. Such catalysts have phosphine ligand cone angles of between about 170° and 180°. Tris(o-methoxyphenyl)phosphine palladium halide and o-trifluoromethylphenyldiphenylphosphine palladium halide catalysts are preferred.

14 Claims, No Drawings

METHOD FOR PRODUCING BRANCHED CARBONYLATION PRODUCTS FROM ALPHA UNSATURATED OLEFINS

FIELD OF THE INVENTION

The present invention relates to methods for making acids and esters from alpha unsaturated olefins using phenyl phosphine palladium halide catalyzed additions of carbon monoxide and water or an alchohol.

BACKGROUND OF THE INVENTION

It has previously been suggested to use certain phenylphosphine palladium halide catalysts in reactions where water, primary alcohols or secondary alcohols together with carbon monoxide are added across ethylenic or acetylenic bonds of a wide variety of organic compounds to form corresponding acids or esters. In U.S. Pat. No. 4,257,973, for example, a method for making carboxylic compounds from aliphatically unsaturated organic compounds is disclosed. This method comprises the catalytic carboxylation or alkoxy carbonylation of the unsaturated compound through the addition of carbon monoxide and a hydroxy compound (preferably having one to four primary or secondary hydroxy groups) or water. According to U.S. Pat. No. 4,257,973, the reaction should be conducted at a temperature 35° C. and 200° C. at pressures of one to one thousand atmospheres in the presence of a catalyst composed of an organophosphorus palladium halide compound and 0.5 to 5 moles per mole of palladium compound of a metallic halide promoter. According to the disclosure U.S. Pat. No. 4,257,973, the preferred organophosphorus palladium halide compound is represented by the formula $(PR_3)_2PdXY$ wherein:

X is chlorine or bromine;
Y is hydrogen, chlorine, bromine, alkyl of 1 to 5 carbon atoms, aralkyl, acyl of 2 to 4 carbon atoms, or aryl of up to 12 carbon atoms;
Each R is selected from lower alkyl, cycloalkyl of 3 to 8 carbon atoms, lower alkoxy, aryl of up to 12 carbon atoms, substituted with up to 3 halogen atoms or lower alkoxy groups, aryloxy groups of up to 12 carbon atoms, arylthio of up to 12 carbon atoms, aralkyl of up to 12 carbon atoms, lower alkylthio, di(lower alkyl) amino pyrrolidino, piperidino and vinyl groups; and
with the proviso that not more than one aryl group attached to phosphorus contains a substituent in a sterically hindered position.

In accordance with U.S. Pat. No. 4,257,973, the promoter should be a chloride of Ti, Tl, Ni, Fe, Cr, Mn, Cu, Pd, Zn or Co or halide compound of Sn.

U.S. Pat. No. 4,257,973 (assigned to Dupont) states that not more than one of the aryl groups should have a "substituent" in a "sterically hindered" position "i.e., in an adjacent [ortho] position on the ring system or in the peri position in the naphthalene series". While U.S. Pat. No. 4,257,973 does not specifically define the type of "substituent" referred to, the only ortho substituted phenyl phosphine palladium catalysts disclosed in this patent have methyl substituents. Both Examples 14 and 16 disclose ortho-methylphenyldiphenylphosphine(o-tolyldiphenylphosphine) catalysts, with and without additions of tin chloride (see Table 1 of U.S. Pat. No. 4,257,973). Uses of these catalysts are reported as resulting in 1 hexene conversions of only 5% and 2% respectively. One of ordinary skill in the art thus recognizes that U.S. Pat. No. 4,257,973 leads away from the use of phenyl phosphine catalysts which exhibit greater steric hinderences than those of these mono o-methyl substituted phenyl phosphines.

It is known that various properties effect the catalytic nature of phosphorus ligands. In "Steric Effects of Phosphorus Ligands In Organometalic Chemistry and Homogenous Catalysis", by Chadwick A. Tolman, *Chemical Reviews* 77:3, 313–348, the electronic and steric effects of changing substituents on phosphorus ligands are discussed in detail. In this article Tolman teaches that catalytic effects caused by changing part of a molecule are electronic, as a result of transmission along chemical bonds, and/or steric, as a result of forces (usually non binding) between parts of a molecule. Tolman discloses that an electronic parameter v may be conveniently used to rank various phosphorus ligands in an electronic series based on CO stretching frequencies, and that v is indeed a measure of such electronic effects. Tolman also discloses that phosphorus ligands can be characterized according to their ligand cone angles (theta) and that the steric parameter is important, at least in those instances where the behavior of a given phosphorus ligand cannot be adequately explained in terms of electronic parameters. Accordingly, Tolman discloses various procedures for calculating the ligand cone angle (theta) of given phosphorus ligands. For example, the phosphine ligand cone angle of o-methylphenyldiphenylphosphine(o-tolyldiphenylphosphine), as calculated using Tolman's method, is 161°. By way of comparison, triphenyl phosphine is calculated to have a phosphine ligand cone angle of only 145°, and tri-o-methylphenylphosphine(tri-o-tolylphosphine) to have a cone angle of 194°.

Heretofore, considerable attention has been directed to the preparation of unbranched carboxylation products. For example, U.S. Pat. No. 3,904,672 discloses the preparation of linear alpha-unsaturated fatty acid derivatives from the reaction of 1-alkynes and carbon monoxide in the presence of a hydroxylated coreactant and a homogenous ligand-stabilized noble metal-group IVb metal halide catalysts complex. Such reactions are described as producing the desired linear, alpha-unsaturated fatty acids or esters in "good yield free from substantial quantities of branched chain and other undesirable by-products".

In U.S. Pat. No. 3,455,989 (1981) entitled "Carbonylation of Olefinically or Acetylenically Unsaturated Compounds", other methods for the production of carboxylic acids or carboxylic esters are disclosed which comprise the use of olefinically unsaturated compounds which are reacted with carbon monoxide and water or alcohols or phenols at elevated temperatures. In this patent, the best results were obtained using phosphines containing at least one aromatic radical, particularly triarylphosphines such as triphenylphosphine, tri-o-cresylphosphine, tri-p-methoxyphenylphosphine, tributylphosphine, diphenylmethylphosphine and phenyldibutyl carboxylic esters.

Isobutyric acid and its esters are valuable intermediates in the synthesis of methyl methacrylate from propylene. The reaction of CO with olefins catalyzed by palladium salts ordinarily gives more straight-chain carboxylic acid products than branched-chain products. The commercial value of reactions producing isobutyric acid depend, however, on the ability of such reactions to achieve high ratios of branched (isobutyric acid) to normal (n-butyric acid) products. Using the phenyl phosphine metal halide catalytic methods many prior art methods have failed to achieve branched to normal ratios of greater than about 2.0–2.6. For example, in German Offenlegunschrift 2,739,096, 90% isobutyric acid ester selectivities were obtained when $AlCl_3$ and HCl were added to a number of arsine-stabilized palladium catalysts, however the highest branched to normal ratio achieved using phosphine ligands was only 2.5. In "Carbonylation of Olefins Under Mild Temperature Conditions in Presence of Palladium Complexes", by Bittler et al, *Angew. Chem.*, Int. Ed. 7:329 (1968), catalytic activities of different palladium salts in olefin carbonylations were reported using bis(triphenylphosphine)palladium dichloride to achieve 60% branched-chain ester and 30% straight-chain ester. Similarly, in U.S. Pat. No. 3,437,676 (1969) both bis(phosphine)palladium dichloride and tetrakis(phosphine)palladium(o) with HCl were reported to be catalysts capable of producing branched-to-normal isomer ratios of approximately 2:1. Lower proportions of branched-to-normal isomers are reported in U.S. Pat. No. 3,723,486 (1:1 mixture of methyl i-butyrate and methyl n-butyrate) and U.S. Pat. No. 3,793,369 (also a 1:1 mixtures of these butyrates). See also G. Cavinato and L. Toniolo, *J. Mol. Catal.* 111 (1979) and *J. Mol. Catal.*, 161 (1981). Other patents disclose techniques which are described or relate to the optimization of straight-chain carboxylic acid products. See U.S. Pat. Nos. 3,530,155; 3,622,607; 3,641,071; 3,641,074; 3,652,655; 3,654,322, 3,661,949; 3,668,249; 3,700,706; 3,906,015; 3,501,518 and 3,968,133. Similarly, in "Noble Metal Catalysis II. Hydrocarbonylation Reaction of Olefins with Carbon Monoxide to Give Saturated Acids", by D. M. Fenton, *J. Org. Chem.*, 38:3192 (1973) the effect of process conditions, solvents, and phosphine ligands on selectivity for normal carbonylation products is described, and a mechanism involving ortho-metallation of the phenyl phosphine ligand is proposed. See also J. F. Knifton, *J. Org. Chem.* 41, 2885 (1976).

Certain methods have been disclosed which lead to high branched-chain carbonylation products. In German Offenlegunschrift 2,701,354 a method is disclosed wherein isopropyl acetate is carbonylated with palladium chloride and a co-catalyst halide to isobutyric acid. Although the selectivity to the branched-chain product is high, the actual isobutyric acid yield is very low, probably due to the instability of the palladium catalyst in the absence of a Group Vb ligand. U.S. Pat. No. 4,245,115 (1981) discloses the conversion of olefins to esters or acids with a high ratio of iso to normal ester or acid by reaction of carbon monoxide with hydroxylic compound in the presence of a palladium salt complex with an arsine or stibine ligand as catalyst.

For descriptions of other carbonylation methods, please refer to G. Cavinato et al, *Chimia*, 33 286 (1979) (phenylphosphine palladium chloride catalyst system used with molecular hydrogen and solvent in propylene carbonylations to improve total ester yield), and to the following papers generally reporting asymmetric hydrocarboxylation of olefins by chiral palladium complexes: Botteghi, et al. *Chimia* 27:477 (1973); Consiglio et al, *Gazz. Chim. Ital.*, 105:1133 (1975); Consiglio, *Helv. Chim Acta.*, 59:124 (1976); Consiglio et al, *Chimia* 30:26 (1976); Consiglio et al, Chimia 30:193 (1976); Consiglio, *J. Organomet. Chem.* 132:C26 (1977); and T Hayashi et al, *Tetr. Lett.* 3925 (1978).

Quite recently, some success has been reported in obtaining high branched product yields using phenyl phosphine catalysts. See U.S. Pat. No. 4,292,437. This patent, which is assigned to Dupont, discloses a process for the preparation of lower alkyl butyrate esters which is described as resulting in a higher percentage of isobutyrate products than has heretore been realized from phosphine liganded palladium catalysts. For example, U.S. Pat. No. 4,292,437 discloses the carbonylation of propylene by contacting the propylene and carbon monoxide with water or a lower alkanol of 1 to 4 carbon atoms in the presence of solvent and a palladium catalyst in complex with a ligand, "which improvement comprises an ortho-substituted ligand of the formula $PAr_3$ wherein ... the Ar moieties bear a total of one or two substituents in positions ortho to one or two carbon phosphorous bonds". (U.S. Pat. No. 4,292,437, Col. 1, lines 30–37, Col. 2, lines 1–3). These substituents are to be selected from lower alkyl or 1–4 carbon atoms, lower alkoxy and phenyl. The ligands are to be provided in a molar ratio to palladium of 4:1 to 122:1 and the process is to be conducted in the presence of a halide acid, such as HCl, HF, HBr or HI.

In U.S. Pat. No. 4,292,437, iso distributions of 81 and 92.5% for o-tolyldiphenylphosphine, of 88.7 and 90.9% for bis(o-tolyl)phenylphosphine, of 92.5 and 91.0% for bis(2,5-dimethylphenyl)phenylphosphine and 92.3 for bis(2,4-dimethylphenyl)phenylphosphine are reported. Tris(o-tolyl)phosphine was reported to give a 91.3% iso distribution product, but to be unstable, resulting in less than one percent propylene conversion. "No significant reaction" was reported for tris(o-anisyl)phosphine[tri-o-methoxyphenylphosphine]. See U.S. Pat. No. 4,292,437, Col. 5–7.

Thus, while some success has recently been achieved in obtaining high branched product yields, the art has yet to fully understand which catalyst and reaction characteristics lead to such yields. As a result, many suitable catalysts for obtaining high branched products yields have been overlooked and/or thought to be unsuitable to achieve such yields.

SUMMARY OF THE INVENTION

Applicants have found that by using compounds exhibiting phosphine ligand cone angles in the range between about 170° and 180°, high yields of branched chain products may be obtained. The preferred embodiment compounds for use in the catalyst systems of the present invention accordingly comprise tris(o-methoxyphenyl)phosphine palladium dichloride, which has a 172° phosphine ligand cone angle, and o-trifluoromethylphenyldiphenylphosphine palladium dichloride, which has a 175° phosphine ligand cone angle. Using o-trifluoromethylphenyldiphenylphosphine palladium chloride, branched to normal ratios of 8.8:1 (88+%) are easily obtained.

The present invention thus provides a novel process for producing carbonylation products comprising high percentages of branched carboxylic acids or esters. The preferred process comprises reacting alpha unsaturated olefins containing between 3 and 24 carbon atoms with carbon monoxide and water or a primary or secondary alcohol in the presence of a catalytic amount of a catalyst system comprised of a palladium compound having the formula:

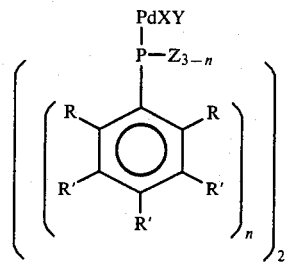

where n is 1, 2 or 3;
where R is selected from hydrogen; methoxy; fluorine; chlorine; cyano; nitro; halo alkyl of 1-5 carbon atoms (particularly fluoro alkyl of 1-5 carbon atoms or chloro-alkyl of 1-5 carbon atoms); dialkyl amino of 1-5 carbon atoms; thioalkyl groups; with the proviso that at least one R is not hydrogen;
where each R' is selected from lower alkyl of 1-5 carbon atoms; lower alkoxy of 1-5 carbon atoms; fluorine; chlorine; phenyl or napthyl, including, substituted derivatives thereof; cyano; nitro; fluoro alkyl of 1-5 carbon atoms, chloro-alkyl of 1-5 carbon atoms; dialkyl amino of 1-5 carbon atoms and thioalkyl groups, and hydrogen;
where X is chlorine, iodine or bromine;
where Y is hydrogen, chlorine, iodine, bromine, lower alkyl aralkyl, or acyl of 2 to 4 carbon atoms or aryl of up to 12 carbon atoms;
where Z is selected from lower alkyl; cycloalkyl of 3 to 8 carbon atoms; lower alkoxy or aryl of up to 12 carbon atoms substituted with up to 3 halogen atoms or lower alkoxy groups; aralkyl groups of up to 12 carbon atoms; arylthio groups or aryloxy groups, each of up to 12 carbon atoms; lower alkylthio; di(lower alkyl)amino; pyrrolidino; piperidino groups and vinyl groups,
with the proviso that the phosphine ligand cone angle of said palladium compound is between 170° and 180°.

Under suitable carbonylation conditions, various halide ions have been found to stabilize and/or enhance the selectivity of the preferred phenylphosphine compounds of the present invention, such that lower P:Pd ratios can be used to produce yields of isobutyric acid of about 90%. For example, the use of o-trifluoromethylphenyldiphenyl palladium bromide has been found to result in highly selective yields and to exhibit an improved stability under the preferred reaction conditions. Accordingly, o-trifluoromethylphenyldiphenylphosphine palladium bromide is the presently preferred phenylphosphine compound for use in the catalyst system of the present invention.

Thus a primary object of the present invention is the provision of a novel process for producing high yields of branched carboxylic acid or esters from alpha-unsaturated olefins.

A further object of the present invention is the provision of a method wherein such olefins are reacted with novel, sterically hindered, ortho-substituted phenylphosphine palladium halide catalysts in the presence of water or primary or secondary alcohols to produce high branched end product yields.

A further object of the present invention is a provision of a novel method for producing high yields of isobutyric acid from propylene, carbon monoxide and water.

These and other objects of the present invention will become apparent from the following, more detailed description.

DESCRIPTION OF THE PREFERRED EMBODIMENTS

Although specific materials and methods are referred to in connection with the following description, one of ordinary skill in the art will recognize that various changes in these materials and methods can be made without departing from the scope of the present invention, which is defined more particularly in the appended claims.

One of the preferred compounds for use in the catalyst system of the present invention is bis(o-trifluoromethylphenyldiphenylphosphine)palladium dichloride. Although the detailed structure of the catalytically active species is not precisely known, this active carbonylation catalyst is easily generated in-situ under reaction conditions using bis(o-trifluoromethylphenyldiphenylphosphine)palladium dichloride, or palladium chloride with an excess of the phosphine ligand as catalyst precursor. Increases in phosphine loading help increase the activity of the palladium catalyst in solution, but decrease the branched chain product selectivity. o-trifluoromethylphenyldiphenylphosphine is not currently available commercially, but can easily be prepared by modifying the synthetic method for tris(trifluoromethylphenyl)phosphine, as reported by Eapen and Tamborski (J. Fluorine Chem., 15:239 (1980). In preparing o-trifluoromethylphenyldiphenylphosphine as used in the following tests, 2-bromobenzotrifluoride (0.16 mole) in anhydrous diethyl ether (200 ml) were placed in a dry four-necked 1000 ml reaction flask fitted with two 125 ml addition funnels, a thermometer and stirrer. n-Butyl lithium (0.15 mole) was placed in one addition funnel while chlorodiphenylphosphine (0.16 mole) dissolved in anhydrous diethyl ether (50 ml) was introduced into a second addition funnel. Dry nitrogen was passed through the flask which was cooled to 0°–5° C. with an ice bath. The n-butyl lithium was added dropwise during 25 minutes while keeping the reaction temperature between 0°–5° C. An exotherm was observed and the contents became reddish-brown in color. After stirring for 30 minutes, the chlorodiphenylphosphine was slowly added for 1 hour. The reaction temperature was maintained at about 5° C. by controlling the rate of addition. At the end of the chlorodiphenylphosphine addition, the contents acquired a brown color. Stirring continued for 2 hours thereafter, whereupon the reaction mixture was hydrolyzed with 6N HCl (200 ml) and the diethyl ether layer was phase separated and dried over molecular sieves overnight. The diethyl ether was evaporated under vacuum to yield the crude phosphine product which was purified by washing with pentane followed by sublimation at 80° C. The final yield of recrystalized o-trifluoromethylphenyldiphenylphosphine was 22 grams (mp=86° C.).

The following examples illustrate the o-trifluoromethylphenyl diphenylphosphine palladium chloride embodiment of the present invention:

EXAMPLE 1 (RUN #125-68)

A 300 ml Hastelloy C autoclave equipped with a magnadrive was charged with 1.5 gms of bis(o-trifluoromethylphenyldiphenylphosphine)palladium dichloride, 8 ml water, and 50 ml of p-dioxane. The system was flushed thoroughly with nitrogen, pressurized with carbon monoxide to 800 psig and heated to 120° C. with stirring. 10 gms of liquid propylene was added and the reaction continued for 18 hours while maintaining the pressure and temperature at 1000 psig and 120° C. respectively. After reaction, the autoclave was cooled and the products analyzed by gas chromatography. Propylene conversion was 46% with an isobutyric acid to n-butyric acid ratio of 8.8:1.

EXAMPLE 2 (RUN #125-104)

Following the procedure of Example 1, 10 gms of propylene were added to 0.3 gms palladium chloride, 10 gms of o-trifluoromethylphenyldiphenylphosphine, 8 ml of water, and 50 ml of p-dioxane at 120° C. and 1000 psig of carbon monoxide. After 3 hours, propylene conversion was 94% with an isobutyric acid to n-butyric acid ratio of 5.7:1.

EXAMPLE 3 (RUN #125-102)

Following the procedure of Example 1, 11 gms of propylene were added to 0.3 gms of palladium chloride, 8 gms of triphenylphosphine, 8 ml of water and 50 ml of p-dioxane at 120° C. and 1000 psig of carbon monoxide. The reaction was shut off after 1.5 hours and the products consisted of isobutyric acid and n-butyric acid with an iso:normal product ratio of 0.28:1.

EXAMPLE 4 (RUN #125-114)

The autoclave was charged with 0.3 gms of palladium chloride, 5 gms o-trifluoromethylphenyldiphenylphosphine, 10 mls of methanol and 50 ml of p-dioxane. After flushing with nitrogen, the autoclave was pressurized with carbon monoxide to 800 psig and heated to 120 degrees C. with stirring. 10 gms of liquid propylene was added and the reaction continued at 120° C. and 100 psig for 3 hours. The autoclave was then cooled and the reaction fluid analyzed by gas chromatography. A methyl isobutyrate:methyl n-butyrate ratio of 7.1:1 was obtained.

EXAMPLE 5 (RUN #125-113)

For purposes of comparison, this example was preformed to test triphenylphosphine under similar reaction conditions. The autoclave was charged with 0.3 gms of palladium chloride, 8 gms of triphenylphosphine, 10 mls of methanol, and 50 ml of p-dioxane. After flushing with nitrogen, the autoclave was pressurized with carbon monoxide to 800 psig and heated to 120° C. with stirring. 11 gm of liquid propylene was added and the reaction continued at 120° C. and 1000 psig for 1.5 hours. The autoclave was then cooled and the reaction fluid analyzed by gas chromatography. The ratio of methylisobutyrate:methyl n-butyrate was only 0.56:1.

The results of Examples 1-5 summarized in the following table:

TABLE I

Carbonylation of Propylene $$C_3^= + CO + ROH \xrightarrow[\substack{R_3P/Pd \sim 18/1 \\ 1000 \text{ psig} \\ 120° C.}]{PdCl_2\ 0.3\ gm} \underset{\text{(branched)}}{\searrow\!\!-CO_2R} + \underset{\text{(normal)}}{\diagup\!\!\diagdown\!\!\diagup\!\!CO_2R}$$

| Ex. | Run # | ROH | Catalyst | Run Time (hours) | P/Pd | Iso:Normal Product Ratio | P—Ligand Cone Angle |
|---|---|---|---|---|---|---|---|
| 1 | 125-68 | H₂O | 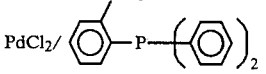 | 18 | 2 | 8.8 | 175° |
| 2 | 125-104 | H₂O | 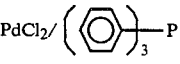 | 3 | 18 | 5.7 | 175° |
| 3 | 125-102 | H₂O | PdCl₂/(C₆H₅)₃P | 1.5 | 18 | 0.28 | 145° |
| 4 | 125-114 | CH₃OH | 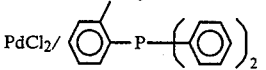 | 3 | 9 | 7.1 | 175° |
| 5 | 125-113 | CH₃OH | PdCl₂/(C₆H₅)₃P | 1.5 | 18 | 0.56 | 145° |

As seen from the above, the use of o-trifluoromethylphenyldiphenylphosphine palladium chloride, under suitable reaction conditions, results in the achievement of high iso to normal product ratios. As evidenced by Examples 1 and 2, higher phosphine to palladium ratios resulted in relatively higher conversion percentages, but relatively lower iso to normal ratios. It is theorized that excess phosphine-ligand loading of the catalyst system leads to catalyst stability, albeit at the expense of iso to normal selectivity.

As described, suitable phenylphosphine palladium halide catalyst for use in the method of the present invention should have phosphine-ligand cone angles of between 170° and 180°. Tris(o-methoxyphenyl)phosphine is another phenylphosphine having a cone angle within this range. This compound has been calculated to have a phosphine ligand cone angle of 172°. Testing of one such catalyst is reported in Example 6.

EXAMPLE 6 (RUN #125-36)

In accordance with the procedure of Example 1, bis(tri-o-methoxyphenyl)phosphine palladium dichloride (0.03M) was introduced into the autoclave with 8 gms of water and 50 mls of dioxane. After flushing with nitrogen, the autoclave was pressurized with carbon monoxide and heated to 120° C. with stirring. 10 gms of liquid propylene was added and the reaction continued at 120° and 1000 psig for 18 hours. The autoclave was then cooled and the reaction fluid analyzed by gas chromatography. An isobutyric:n-butyric acid ratio of 3.2:1 was obtained.

EXAMPLE 7 (RUN #125-15)

By way of comparison, di-o-tolylphenylphosphine, which has a phosphine ligand cone angle of 178°, was also tested. Following the procedure of Example 6, bis(di-o-tolylphenylphosphine)palladium dichloride was reacted for 80 minutes under corresponding reaction conditions to produce a conversion of propylene of 89% and an isobutyric:n-butyric acid ratio of 5.4.

The results of Examples 1 and 6 are compared to similar propylene to isobutyric/n-butyric acid conversion tests which were performed using catalysts not within the scope of the present invention. The results of these tests are summarized in Table II:

TABLE II

Carbonylation of Propylene $$C_3^= + CO + H_2O \xrightarrow[\text{dioxane 50 ml}]{[Pd] = 0.03M} \underset{\text{IBA}}{\text{CO}_2\text{H}} + \underset{\text{NBA}}{\text{CO}_2\text{H}}$$

10 g    8 g    1000 psig, 120° C.

| Example | Run # | Catalyst | P—Ligand Cone Angle | Run Time | % Conversion | IBA/NBA Ratio |
|---|---|---|---|---|---|---|
| 1 | 125-68 | 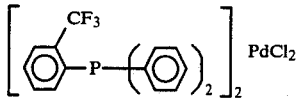 | 175° | 18 hours | 46% | 8.8 |
| 6 | 125-36 | 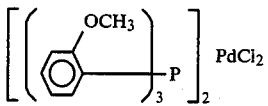 | 172° | 18 hours | 84% | 3.2 |
| 7** | 125-15 | 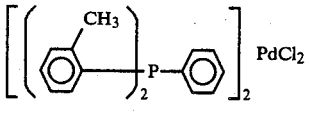 | 178° | 80 minutes | 89% | 5.4 |
| 8 | 125-22 | 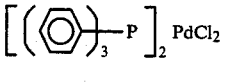 | 145° | 40 minutes | 93% | 1.0 |
| 9 | 125-38 | 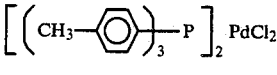 | 145° | 30 minutes | 86% | 1.1 |
| 10 | 125-37 | 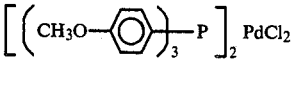 | 145° | 30 minutes | 81% | 1.1 |
| 11 | 125-16 | 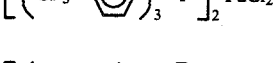 | 145° | 30 minutes | 91% | 2.2 |
| 12 | 125-46 | 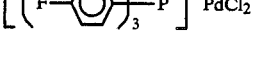 | 145° | 25 minutes | 83% | 1.4 |
| 13 | 125-13 | 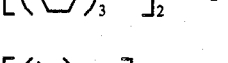 | 170° | 90 minutes | 67% | 1.5 |
| 14 | 125-12 | 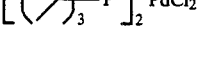 | 160° | 90 minutes | 79% | 1.4 |
| 15 | 125-42 | 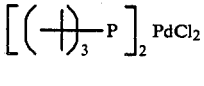 | 182° | 18 minutes | 44% | 0.90 |

TABLE II-continued
Carbonylation of Propylene $$C_3^= + CO + H_2O \xrightarrow[\text{dioxane 50 ml}]{[Pd] = 0.03M} \underset{\text{IBA}}{\overset{CO_2H}{\bigwedge}} + \underset{\text{NBA}}{\overset{}{\bigwedge\!\!\!\bigvee\!\!\!{}^{CO_2H}}}$$

10 g     8 g     1000 psig, 120° C.

| Example | Run # | Catalyst | P—Ligand Cone Angle | Run Time | % Conversion | IBA/NBA Ratio |
|---|---|---|---|---|---|---|
| 16 | 125-48 | 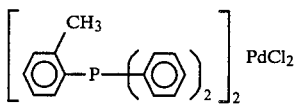 | 161° | 30 minutes | 85% | 2.6 |
| 17 | 125-40 | 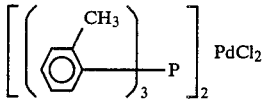 | 194° | 18 hours | little conversion of propylene | |
| 18 | 125-34 | 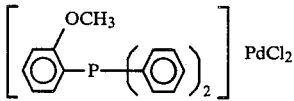 | 154° | 60 minutes | 92% | 2.6 |
| 19 | 125-51 | 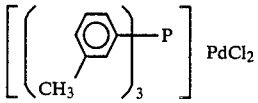 | 150° | 30 minutes | 94% | 1.1 |
| 20 | 125-5 | (diphos) PdCl$_2$ | — | 18 hours | no reaction | |
| 21 | 125-24 | 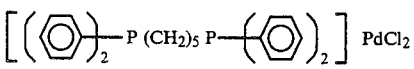 | — | 18 hours | 85% | 0.44 |
| 22 | 125-20 | 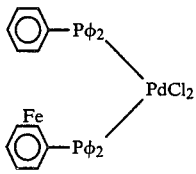 | — | 18 hours | 80% | 0.66 |
| — | see Ref 1 | 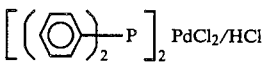 | — | NA | NA | 2.0* |
| — | see Ref 2 | 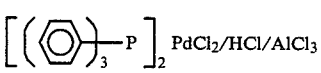 | — | NA | NA | 2.5* |

*Ratios indicated are branched-chain ester/straight-chain ester since carbonylations were carried out in the presence of alcohols.
**See also Examples 3 and 4 of U.S. Pat. No. 4,292,437
Ref 1   K. Bittler, N. Kutepow, D. Nuebauer, and H. Reis, Angew. Chem. Int. Edit., 7, 329(1968).
Ref 2   Ger. Offen. 2,739,096 (March 2, 1978 to Dupont).

From the above, it will be seen that the compounds of Examples 7, 13 and 15 (runs 125-15, 125-13 and 125-42) have phosphine ligand cone angles within the above-described 170°-180° range, however, these catalysts, are either not phenylphosphine catalysts and/or do not otherwise satisfy the above-specified requirements for a compound useful in catalytic system of the present invention. The other compounds listed in Table II, although containing similar phenyl substituents to those of the preferred embodiment compounds, do not have ligand cone angles within the preferred ranges, and do not achieve the desired high ratios of IBA to NBA.

For purposes of comparison, Table III lists the phosphine ligand cone angles of various phenylphosphine compounds. From this table it will be seen that phosphine ligand cone angles in the range of 170°-180° will result from between 1 to 3 or more ortho substitutions. Accordingly, the teaching of U.S. Pat. No. 4,292,437 that the ligands should have one or two ortho substituents may be correct when those substituents are lower alkyl groups, but is clearly incorrect at least when those groups are methoxy groups. As seen from Example 6 (Table II and III), bis(tri-o-methoxyphenyl)phosphine palladium dichloride achieved an 84% conversion with an iso:normal ratio of 3.2:1. It is suspected that the test of this compound attempted in U.S. Pat. No. 4,292,437 and reported as having "no significant reaction", may have failed due to the selected reaction conditions, including perhaps the use of trifluoroacetic acid in this test. See Example 10 of U.S. Pat. No. 4,292,437.

TABLE III

| Example | Compound | Phosphine Ligand Cone Angle |
|---|---|---|
| 23 | 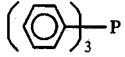 | 145° |
| 24 | 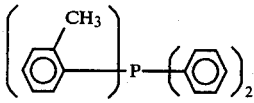 | 161° |
| 25 | 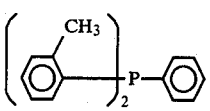 | 178° |
| 26 | 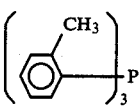 | 194° |
| 27 | 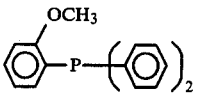 | 154° |
| 28 | 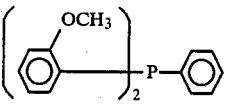 | 163° |
| 29 | 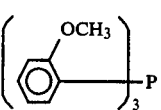 | 172° |
| 30 | 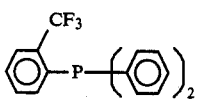 | 175° |
| 31 | 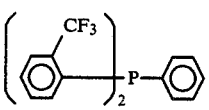 | 205° |
| 32 | 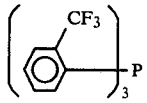 | 235° |

As discussed above, it is desired to provide a catalyst which is stable under the selected reaction conditions, but which nonetheless results in a high branched to normal product selectivity. Although exhibiting high selectivities for branched products, the palladium catalysts utilized in Examples 1 and 7 (Runs #125-15 and #125-68), as reported in Table II above, were less than completely stable under the specified carbonylation conditions. In fact, considerable amounts of palladium metal were found to have precipitated out from the reaction solution during these runs. While catalyst stability can be dramatically improved by adding excess phosphine ligand, branched product selectivities have been found to decrease with increasing phosphine loading (in Table IV compare Run #87-144 with 125-15 and Run #125-104 with 125-68). Similar detrimental effects of ligand concentration on the branched to normal isomer ratio have also been observed using the triphenylphosphine/palladium chloride catalyst system described by G. Cavinato and L. Toniola, *J. Mol. Catal.*, 161 (1981). Accordingly, one of the objects of the present invention is to further provide catalysts which not only produce high-yields of branched-chain products, but catalysts which can achieve such selectivities under conditions which do not result in the precipitation of the catalyst from the reaction solution.

It is well known in the art that phosphine stabilized palladium bromide complexes may be provided, however such complexes are known to be less effective carbonylation catalysts than the analgous palladium chloride complexes. See for example K. Bittler, et al, *Angew. Chem. Int. Ed.*, 7:329 (1968) and U.S. Pat. No. 3,437,676 (1969).

In order to investigate the effects of providing palladium bromide complexes of the phosphine ligands of the present invention, the experiments summarized in Table IV were performed.

TABLE IV

Propylene Carbonylation to IBA

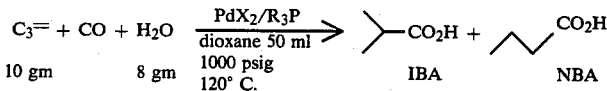

| Example | Run # | Catalyst | P/Pd | Reaction Time | % Conversion | IBA:NBA Ratio |
|---|---|---|---|---|---|---|
| 1 | 125-68 | 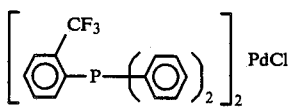 | 2 | 18 hrs. | 46% | 8.8 |
| 2 | 125-104 | 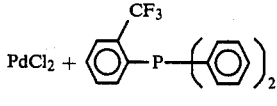 | 18 | 3 hrs. | 94% | 5.7 |

TABLE IV-continued
Propylene Carbonylation to IBA $$C_3^= + CO + H_2O \xrightarrow[\substack{\text{dioxane 50 ml} \\ \text{1000 psig} \\ 120°\text{ C.}}]{PdX_2/R_3P} \text{>}-CO_2H + \diagdown\!\diagup\!\!\diagdown CO_2H$$

10 gm     8 gm     IBA     NBA

| Example | Run # | Catalyst | P/Pd | Reaction Time | % Conversion | IBA:NBA Ratio |
|---|---|---|---|---|---|---|
| 3 | 125-102 | 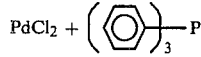 | 18 | 1.5 hrs. | 58% | 0.28 |
| 7 | 125-15 | 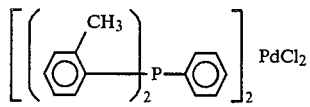 | 2 | 1.5 hrs. | 89% | 5.4 |
| 8 | 125-22 | 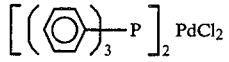 | 2 | 0.75 hr. | 93% | 1.0 |
| 37 | 87-144 | 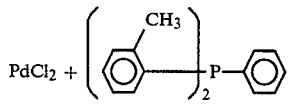 | 20 | 1.5 hrs. | 89% | 2.6 |
| 38 | 125-106 | 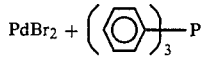 | 18 | 3 hrs. | 27% | 0.37 |
| 39 | 125-107 | 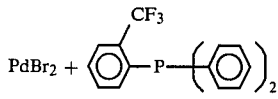 | 18 | 3 hrs. | 95% | 8.7 |
| 40 | 125-109 | 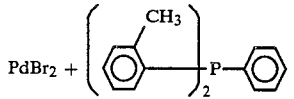 | 18 | 1 hr. | 79% | 7.4 |
| 41 | 125-105 | 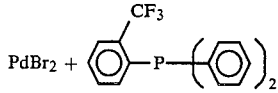 | 9 | 3 hrs. | 94% | 9.4 |
| 42 | 125-108 | 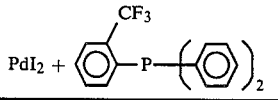 | 19 | 3 hrs. | 95% | 5.1 |

As seen from Examples 3 and 38 (Run #125-106, and 125-102), the above-described effects of bromide vs. chloride palladium complexes is confirmed for the triphenylphosphine ligand, that is, propylene carbonylates at a lower rate and gives more metallic palladium deposit when the triphenylphosphine palladium bromide catalyst is used than when the corresponding triphenylphosphine palladium chloride catalyst is used. Quite surprisingly, however, it has been found that palladium bromide in the presence of excess o-trifluoromethylphenyldiphenylphosphine gives a 90% IBA yield without catalyst decomposition (Run #125-107). Palladium bromide with di-o-tolylphenylphosphine also carbonylates propylene selectively to IBA, however the selectivity was found to be lower than with o-trifluoromethylphenyldiphenylphosphine, and some catalyst decomposition to metallic palladium was observed using this compound during Example 40 (Run #125-109). As shown in Example 41 (Run #125-105), the isobutyric acid:n-butyric acid ratio in an o-trifluoromethylphenyldiphenylphosphine/palladium bromide catalyst system can be further improved from 8.7:1 to 9.4:1 by decreasing the phosphine loading, however, at this phosphine concentration level, some catalyst will tend to decompose to metallic palladium. Such catalyst decomposition was not observed in Example 42 (Run #125-108) with o-trifluoromethylphenyldiphenylphosphine/palladium iodide catalyst, however IBA selectivity was found to be only 84%.

It has accordingly been concluded that these halides exhibit different effects on catalyst stability depending upon the nature of the particular ligand. For triphenylphosphine, the chloride and iodide species result in better catalyst stability than the bromide species, and the chloride species resulted in lower IBA selectivities than either of the other two halide species. For di-o-tolylphenylphosphine, each of these halides had about the same effect on catalyst stability, however the highest IBA selectivities were obtained with the bromide species, which was superior to the selectivity obtained with the iodide species which in turn showed an improvement over the selectivity achieved using the chloride species. For o-trifluoromethylphenyldiphenyl phosphine, the bromide and iodide species were both superior to the chloride species in terms of catalyst stability, however the bromide species was found to be superior to either the chloride or the iodine species in terms of IBA selectivity.

In performing the process of the present invention it is thus preferred to provide an excess of the phosphine ligand which is at least sufficient to prevent decomposition of substantial amounts of said palladium compound during said process. Under normal conditions, a substantial amount is considered to be ten percent or more of the palladium. It is further desired to minimize phosphine loading to increase the branched to normal product ratio. In this regard, the phosphine loading should not be so great as to reduce the iso to normal ratio by more than about 50%, and in most instances should be just sufficient to prevent decomposition of substantial amounts of catalyst.

In view of the foregoing description, one of ordinary skill in the art will recognize the various changes may be made in the materials and methods described herein without departing from the scope of the present invention. For example, one of ordinary skill in the art will recognize that the phenyl group of the specified catalyst should not be substituted with too many electron drawing groups, since such substitutions may adversely affect the phosphine binding and thus destabilize the palladium catalyst. Such electron withdrawing groups include $CF_3$ and F. Accordingly, it is presently anticipated that no more than $2CF_3$ or 3F groups should be substituted on any single phenyl group of the phosphine ligand.

We claim:

1. A process for making branched carboxylic acids or esters which comprises reacting an alpha unsaturated olefin containing between 3 and 24 carbon atoms with carbon monoxide and water or a primary or secondary alcohol in the presence of a catalytic amount of a catalyst composed of a palladium compound having the formula:

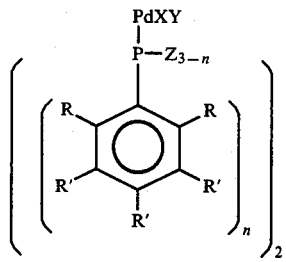

wherein n is 1, 2 or 3;

where R is selected from hydrogen, methoxy; and trifluoromethyl, with the provisos that at least one R is not hydrogen and when an R group is methoxy, n equals 3, and in each of the phenyl rings attached directly to phosphorus, one R group is methoxy and the other R group is hydrogen;

where each R' is selected from lower alkyl of 1 to 5 carbon atoms; lower alkoxy of 1 to 5 carbon atoms; fluorine; chlorine; phenyl or naphthyl, cyano; nitro; fluoro alkyl of 1 to 5 carbon atoms; chloroalkyl of 1 to 5 carbon atoms; dialkyl amino of 1 to 5 carbon atoms and thioalkyl groups, and hydrogen;

where X is chlorine, iodine, or bromine;

where Y is hydrogen, chlorine, iodine, bromine, lower alkyl, aralkyl, acyl of 2 to 4 carbon atoms or aryl of up to 12 carbons;

where Z is selected from lower alkyl, cycloalkyl of 3 to 8 carbon atoms, lower alkoxy or aryl of up to 12 carbon atoms, arylthio groups or aryloxy groups, each of up to 12 carbon atoms, lower alkyl-thio, di(lower alkyl)amino, pyrrolidino, piperidino and vinyl, with the further proviso that the phosphine ligand cone angle of said palladium compound is between 170° and 180°.

2. The process of claim 1 wherein X and Y are bromine.

3. The process of claim 1 wherein one R group is trifluoromethyl.

4. The process of claim 3 wherein n equals 1 and Z is phenyl.

5. The process of claim 4 wherein each R' and the remaining R are hydrogen.

6. The process of claim 1 wherein said olefin is propylene.

7. The process of claim 1 wherein the molar ratio of water to olefin is 1:1 to 1:2.

8. The process of claim 1 wherein said method further comprises the step of introducing an inert diluent during said reaction.

9. The process of claim 8 wherein said inert diluent is $CO_2$.

10. The product of claim 1 wherein an excess of the phosphine ligand of said palladium compound is present, said excess being at least sufficient to prevent decomposition of ten percent or more of said palladium compound during said process.

11. The method of claim 1 wherein in said formula n equals 3, and in each of the phenyl groups directly attached to phosphorus one of said R groups is methoxy and the other is hydrogen.

12. The method of claim 11 wherein in said formula each R' is H.

13. The method of claim 1 wherein an excess of the phosphine ligand of said palladium compound is present said excess providing a phosphine to palladium ratio of 2:1 to 19:1.

14. The method of claim 13 wherein said ratio is about 9:1.

* * * * *